United States Patent [19]
Zofchak et al.

[11] Patent Number: 5,972,324
[45] Date of Patent: Oct. 26, 1999

[54] MONOHYDRIC ALCOHOL DERIVED URETHANES AND THEIR USE IN COSMETIC FORMULATIONS

[75] Inventors: Albert Zofchak, Matawan; Madeline Kenney, Caldwell; John Obeji, Clifton; Michael Mosquera, Forked River, all of N.J.

[73] Assignee: Alzo, Inco., Sayreville, N.J.

[21] Appl. No.: 08/788,162

[22] Filed: Jan. 24, 1997

[51] Int. Cl.[6] .......................... A61K 31/74; A61K 31/66; A61K 7/06

[52] U.S. Cl. ................. 424/78.03; 424/70.1; 424/70.11; 424/70.16; 424/78.02; 424/61; 424/64; 424/69; 514/148; 514/937; 514/944; 514/478; 514/479

[58] Field of Search .......................... 106/169.39, 169.33, 106/170.28, 182.22, 183.1; 132/202, 221, 209; 560/265, 231, 248; 520/319, 323.1; 524/198, 601; 424/449, 47.71, 69, 61, 64, 70.1, 70.11, 70.16, 78.02, 78.03; 514/148, 944, 937, 478, 479

[56] References Cited

U.S. PATENT DOCUMENTS

| | | |
|---|---|---|
| 4,971,800 | 11/1990 | Chess et al. . |
| 5,045,317 | 9/1991 | Chess et al. . |
| 5,051,260 | 9/1991 | Chess et al. . |
| 5,707,612 | 1/1998 | Zofchak et al. .......................... 424/69 |

FOREIGN PATENT DOCUMENTS

| | | |
|---|---|---|
| 2 557 576 | 7/1985 | France . |
| 1179231 | 1/1970 | United Kingdom . |

*Primary Examiner*—Lynette F. Smith
*Assistant Examiner*—Datquan Lee
*Attorney, Agent, or Firm*—Henry D. Coleman; R. Neil Sudol

[57] ABSTRACT

The present invention relates to a dimeric urethane compounds derived from monohydric alcohols, generally fatty alcohols, and a diisocyanate according to the following reaction scheme:

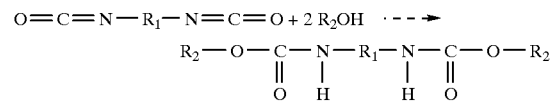

wherein $R_1$ is selected from the group of saturated or halogen substituted linear, cyclic or branch-chained hydrocarbons and $R_2$ is a linear, cyclic or branch-chained alkyl or aminoalkyl group ranging from two to 200 carbon atoms, preferably two to 50 carbons, more preferably 6 to 36 carbons, said urethane compound being substantially free from terminal hydroxyl groups.

20 Claims, No Drawings

MONOHYDRIC ALCOHOL DERIVED URETHANES AND THEIR USE IN COSMETIC FORMULATIONS

FIELD OF THE INVENTION

The present invention is directed to novel compositions of urethane emollients, solubilizers, clarifiers and emulsifiers derived from monohydric alcohols and having no free isocyanate groups. These urethane emollients are substantially free of terminal hydroxyl groups and are derived from linear, branch-chained or aromatic monohydric alcoholic compounds of synthetic or natural origin.

BACKGROUND OF THE INVENTION

Standard emollients for the cosmetic, toiletry and personal care industries have been esters (monohydric) such as isopropyl myristate, butyl stearate, cetyl octanoate and isostearyl isostearate covering a wide breadth of molecular weights. Monohydric esters have also been manufactured from high molecular weight compounds such as behenic acid and behenyl alcohol which yield a solid ester useful as an emollient for increasing the melting point characteristics of a given formulation. Synthetic spermacetic waxes have been utilized for the past thirty years to replace the natural rare variety. Such products as cetyl palmitate, cetyl myristate and mixed cetyl esters have essentially replaced the use of spermacetic wax.

In the mid-seventies, there was a critical shortage of beeswax, and the synthesis of a synthetic version of this natural wax and emollients derived from this wax was sought. As one solution, the relatively high molecular weight dodecanedicarboxylic acid was esterified with a mixture of cetyl, stearyl and polyoxyethylene glycols to render a product that was found to be a suitable replacement. With the mixture of relatively high molecular weight alcohols and polyethers, the dicarboxylic acid of $C_{12}$ yielded a perfectly usable product for skin applications-where natural beeswax had been used for numerous years.

For many years, monohydric alcohol diesters used in the cosmetic and personal care industries have been synthesized from such difunctional carboxylic acids as adipic, sebacic, azeleic, dodecanedicarboxylic acid and dimer acid, as well as anhydrides such as maleic, succinic and phthallic, among others. Based on the molecular weight of the difunctional carboxylic acid and the alcohol used, it was possible for the synthetic organic chemist to obtain a wide range of properties from these compositions, including, for example, dryness, oiliness, spreadability, lubricity, freezing point depression, insect repellency (e.g., dicapryl adipate), melting and slip point modification, emulsion synergism, solvency and color dispersion.

As the molecular weight of the dicarboxylic acid and corresponding alcohol increase, a greater degree of heaviness is imparted to the emollient, along with a higher degree of viscosity. As the degree of unsaturation of the alcohol used increases and becomes more olefinic in character, spreadability is enhanced. For example, diesters derived from oleyl or linoleyl alcohols have a greater degree of spreadability than does a corresponding diester derived from stearyl or isostearyl alcohol.

It is possible to further influence the melting point and indeed the viscosity of a diester through the use of branched rather than linear structures. With the introduction of an ether linkage, the liquidity of a given diester is also enhanced. Diesters made from ethoxylated and/or propoxylated adducts of alcohols have also been used as emollients and emulsifiers.

As a result of molecular weight and structure, diisopropyl adipate has been found to be an extremely dry ester with excellent solvency characteristics. Because of its physical properties, diisopropyl adipate finds use in products ranging from floating bath oils, after shaves, creams, lotions, deodorants, pre-electric shave lotions, to antiperspirants. Diisopropyl adipate has been widely used for numerous years in these applications because of the availability of raw materials and relatively low production cost. Diisostearyl adipate, on the other hand, is a relatively heavy, water white diester with little or no odor that imparts a luster and sheen to the skin and, as a result of its molecular weight and viscosity, has a tendency to linger on the skin. Dicapryl adipate is a diester derived from natural sources (through the cracking of castor oil to yield caprylene, then conversion to the corresponding alcohol) which has been found to exhibit insect repellency and has met with huge success in repellents for use in human and animal products. Diesters derived from dimer acids, such as diisopropyl dimerate and diisostearyl dimerate, in addition to being excellent, long lasting emollients because of their relatively high molecular weight, were shown to add anti-irritation characteristics to given skin formulations.

Typical end-use applications of diesters of dicarboxylic acids in the personal care, cosmetic as well as toiletry industries include: skin care products, eye makeups, body shampoo, stick deodorants, protective skin formulations, lipsticks, lip glosses, pre-electric and after shave lotions, after-bath splashes, shampoos and rinses, presun and sun products, antiperspirants and sunscreens.

OBJECTS OF THE INVENTION

It is an object of the present invention to provide novel and unique urethanes of monohydric alcohols which are substantially free of terminal hydroxy groups as emollients in cosmetic, toiletry and personal care products.

It is a further object of the present invention to provide urethanes of monohydric alcohols as emulsifiers for use in the cosmetic, toiletry and personal care area.

It is another object of the present invention to provide novel urethanes of monohydric alcohols that are resistant to pH variable and thermal degradation that is commonly associated with mono- and diesters.

It is yet another object of the present invention to introduce novel and unique urethanes of monohydric alcohols which are substantially free of terminal hydroxyl groups which function as vehicles to increase adhesion in given formulations in the cosmetic, toiletry and personal care industry.

It is still another object of the present invention to introduce novel and unique urethanes of monohydric alcohols which are substantially free of terminal hydroxyl groups which will function to modify melting points in the cosmetic, toiletry and personal care products.

It is yet a further object of the present invention to introduce novel and unique urethanes of monohydric alcohols which are substantially free of terminal hydroxyl groups which will be soluble in silicone fluids commonly used in the personal care, cosmetic and toiletry industries.

It is still a further object of the present invention to introduce novel and unique urethanes of monohydric alcohols which are substantially free of terminal hydroxyl groups to act as vehicles for functional additives such as organic and inorganic sunscreens, vitamins and protein hydrolysates, among numerous others.

These and/or other objects of the invention may be readily gleaned from the description of the invention, which follows.

SUMMARY OF THE INVENTION

The present invention relates to a dimeric urethane compounds derived from monohydric alcohols, generally fatty alcohols, and a diisocyanate according to the following reaction scheme:

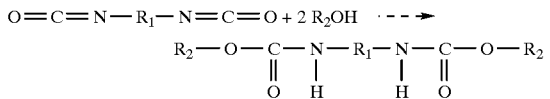

wherein $R_1$ is selected from the group consisting of saturated, unsaturated, aromatic or halogen substituted linear, cyclic, aromatic or branch-chained hydrocarbons and $R_2$ is a linear, cyclic, aromatic, branch-chained alkyl, aminoalkyl, amino alkanol or alkoxide group ranging from two to 500 carbon atoms, preferably two to 50 carbons, more preferably 6 to 36 carbons, said urethane compound being substantially free of terminal hydroxyl groups.

Compounds according to the present invention exhibit primary utility as emollients, wetting agents, dispersants, lubricants, plasticizers, stabilizers, emulsifiers, clarifying agents, solubilizing agents and adhesion and melting point modifiers in formulations of cosmetic, toiletry and personal care products. The emollient properties of compounds according to the present invention are primarily due to the hydrophobic nature of the fatty alkyl groups, which maintain a desirable moisture balance as it softens and soothes the skin and related mucous membranes.

By proper selection of the diisocyanate and monohydric alcohol, it is possible to obtain a wide variety of properties in the resultant urethane compound, ranging from such characteristics as a grasslike, resinous product suitable as an extremely heavy emollient and replacement for diisostearyl adipate to a solid product such as an arichidyl urethane suitable as a substitute for beeswax in formulations. The monohydric alcohols reacted to produce the compounds with a diisocyanate group according to the present invention may be synthetically or naturally derived.

One of the more innovative properties of compounds according to the present invention is the stability of the dimeric urethane of the monohydric alcohols over a wide pH range and temperature. Under conditions causing the prior art diesters of corresponding alcohols to readily decompose, their urethane counterparts will remain relatively stable. Consequently, the dimeric urethanes are versatile in their chemical properties, and are unique in their ability to resist hydrolysis and thermal decomposition. Stable storage compounds (those which are resistant to degradation at variable pH or at elevated temperature) may be readily formulated using compounds according to the present invention.

Other properties of the compounds of the present invention which make them superior to the diesters currently used may include:

Water-white color;

Extremely low order of irritation and toxicity;

Substantial absence of hydroxyl groups;

Excellent compatibility in cosmetic and toiletry formulations;

Solubility in sunscreens, i.e., octacrylene, octyl salicylate, octylmethoxy cinnamate, menthyl anthranilate, PABA;

Solubility in mineral oil;

Solubility in vegetable oil;

Solubility in silicone fluids;

Solubility in most esters;

Solubility in most alcohols;

Essentially odorless;

Substantially Non-rancidifying.

Another aspect of the present invention relates to compositions comprisng the previously described urethane compounds in combination with about 0.5% to about 100% by weight of a free or unreacted monohydric alcohol. The inclusion of the monohydric alcohol may be used as a viscosity control additive or as a solubilizing agent in this aspect of the present invention. Thus, in this aspect of the present invention, a composition for use in cosmetic, toiletry and personal care products consists essentially of about 0.25% to about 50% by weight of a free monohydric alcohol and about 50% to about 99.75% by weight of a urethane compound according to the present invention. Preferably, the composition according to this aspect of the present invention consists essentially of about 0.5% to about 25% by weight, more preferably about 1% to about 15% by weight free monohydric alcohol.

Urethane compounds according to the present invention may be used in personal care, toiletry or cosmetic compositions in amounts ranging from about 0.05% to about 35% by weight, preferably about 0.5% to about 25% by weight, more preferably about 1% to about 15% by weight of the final personal care, toiletry or cosmetic composition. Urethane compounds according to the present invention find particular use in compositions which utilize pH variability or heat for manufacturing or utilize elevated temperatures during use (for example, in the case of shampoos, conditioners, sunscreens, etc.). Storage stability of the final composition is another feature which may be markedly improved by the inclusion of effective amounts of the present compounds.

DETAILED DESCRIPTION OF THE INVENTION

The term "monohydric alcohol" is used throughout the specification to describe a linear, cyclic, aromatic or branch-chained hydrocarbon having a single hydroxy group located at one terminus of the molecule and/or a linear, cyclic or branched-chain amine having a single hydroxy group located at one terminus of the molecule and includes such amine-containing compounds as monoethanolamine, aminoethylethanolamine, amidoamines, diglycolamine, acetylated monoethanolamine, among numerous others. The amine may be a primary, secondary or tertiary amine. The compounds may be unsubstituted or halogen substituted. The inclusion of an amine may be advantageously employed because of the tendency of the amine to substantially protonate and become more water soluble at pH's below about 10.0. In addition, the presence of the amine group, due to its cationic nature, imparts a more substantive character to the compound. In a preferred embodiment of the present invention, the length of the monohydric alcohol is between 2 and 200 carbons. In more preferred embodiments, the monohydric alcohol ranges from about 2 to about 50 carbons and in even more preferred embodiments, the monohydric alcohol ranges from about 6 to about 36 carbons. Exemplary monohydric alcohols for use in the present invention include, range for example, from ethyl through $C_{50}$ alcohols, more preferably $C_6$ through $C_{36}$ and include, for example, ethanol, isopropanol, butanol, isobutanol, amyl alcohol, isoamyl alcohol, hexanol, isohexanol, heptanol, n-octanol, 2-ethylhexanol, isooctanol, n-nonanol, isononyl alcohol, n-decanol, isodecanol, n-lauryl alcohol, tridecanol, n-myristyl alcohol, n-cetyl alcohol, isocetyl alcohol, n-stearyl, isostearyl alcohol, octyldodecanol, archidyl alcohol, alcohols up through $C_{50}$, more preferably up to $C_{36}$, ethoxylated and/or propoxylated versions of the above-described alcohols, phenoxyethanols and ethoxylated and/or propoxylated nonyl phenols. Numerous additional monohydric alcohols also may be used in the present invention.

The term "diisocyanate" is used throughout the specification to describe a linear, cyclic or branch-chained hydrocarbon having two free isocyanate groups. The term "diisocyanate" also includes halogen substituted linear, cyclic or branch-chained hydrocarbons having two free isocyanate groups. Exemplary diisocyanates include for example, isophorone diisocyanate, m-phenylenediisocyanate, p-phenylene diisocyanate, 4,4-butyl-m-phenylene diisocyanate, 4-methoxy-m-phenylene diisocyanate, 4-phenoxy-m-phenylene diisocyanate, 4-chloro-m-phenylene diisocyanate, toluenediisocyanate, m-xylylenediisocyanate, p-xylylenediisocyanate, 1,4-napthalenediisocyanate, cumene-14,-diisocyanate, durenediisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphylenediisocyanate; 2,4-diphenylhexane-1,6-diisocyanate; methylenediisocyanates; ethylenediisocyanates; trimethylenediisocyanate, tetramethylenediisocyanate, pentamethylenediisocyanate, hexamethylenediisocyanate, nonamethylenediisocyanate, decamethylenediisocyanate, 3-chloro-trimethylenediisocyanate and 2,3-dimethyltetramethylene diisocyanates.

The term "emollient" is used throughout the specification to describe compounds according to the present invention which soften, lubricate and moisturize the skin as as well as sooth irritation to the skin and mucous membranes, i.e., they are soothing to the skin.

The term "emollient effective amount" is used throughout the specification to describe concentrations or amounts of compounds according to the present invention which are included in cosmetic and personal care products according to the present invention which provide effective emollient character for treating keratinous and epithelial tissue, including skin, nails (ungual tissue), hair and mucous linings of the mouth and nasal passages.

The term "effective amount" is used throughout the specification to describe concentrations or amounts of compounds according to the present invention which are effective in conveying desired traits such as emulsification, clarification, adhesion, melting point modification or solubility to a formulation of a cosmetic, toiletry or personal care product.

The term "substantially free' is used throughout the specification to describe preferred urethane compounds according to the present invention which essentially contain no free terminal hydroxyl groups, i.e., they appear to be all reacted and analytical methods do not detect terminal hydroxyl groups other than those which may appear as slight impurities in the compounds of the present invention. The term "substantially free" is not a theoretical absolute value, but merely reflects the practical limits of detecting free terminal hydroxyl groups in the present invention.

Compounds according to the present invention may be prepared by synthetic methods known in the art. A general synthetic scheme involves reacting at least two molar equivalents of a monohydric alcohol, generally a fatty alcohol, with a diisocyanate in the presence of heat and a catalyst such as stannous octanoate. Each isocyanate moiety is thereby converted to a urethane moiety with the aliphatic portion of the alcohol extending out from the urethane moiety. The free alcohols are all reacted with isocyanate groups to form urethanes, leaving substantially no free hydroxyl groups at the ends of the side chains (i.e. the compounds of the present invention are not hydroxyl-terminated). Preferably, there are no free hydroxyl moieties anywhere on the side chains of the compounds of the present invention. Illustrative examples of the synthesis of particular compounds follow below.

Compounds according to the present invention may be used as emollients for keratinous and epithelial tissue such as hair, ungual tissue (nails), skin and related mucous membranes. By addition of an emollient effective amount of these urethanes, formulations for use as cosmetic, toiletry or personal care products will acquire the desirable soothing characteristics.

Effective amounts of the urethanes of the present invention may also serve as emulsifiers, clarifiers and melting point modifiers in formulations of the personal care, cosmetic and toiletry industries, especially where diesters of dicarboxylic acid have been used in the past or in formulations of silicone fluids, in which these novel urethanes are soluble. The urethanes of the present invention have superior stability at high or low pH values and thermal variations, where the mono- and diesters of the prior art are subject to degradation. Consequently, the dimeric urethanes of the present invention provide a significantly greater degree of stability and flexibility in formulations than do the diesters. It is an unexpected result that the urethane compounds of the present invention would provide the variety of characteristics exhibits with a high degree of stability (to variations in pH and temperature). In addition, the present compounds are compatible with biological systems and are generally substantially non-toxic (i.e., they can be used safely in cosmetic, toiletry and personal care products).

The present compounds instill a great degree of flexibility in formulating personal care products. The viscosity of a formulation for cosmetic, toiletry or personal care use can be dictated by adding an effective amount of a compound of the present invention with an appropriate length side chain. Shorter side chains, i.e., those derived from monohydric alcohols of about 1 to 3 carbon atoms product materials of a resinous consistency. Side chains of 6 to 10 carbon atoms produce compounds of lower viscosity, with maximum viscosity of approximately 1000 centipoise units. Longer side chains containing monohydric alcohols of about 12 to 500 carbon atoms lead to higher viscosity, with compounds containing about 6 to 24 carbon atoms leading to viscosities within the range of approximately 4000 to 5000 centipoise units. Those of ordinary skill engaging in routine experimentation will be able to readily identify the proper side chain length for any desired viscosity. Similarly affecting the viscosity and adhesion is the degree of branching of the side chains of the urethane; with increasing branching for the same number of carbon units, the viscosity decreases. In addition, as the amount of unsaturation in a side chain increases, the viscosity of the dimeric urethane from which such monohydric alcohol is derived will decrease. The ideal properties of emmolience are anticipated in compounds according to the present invention where the monohydric alcohol (side chain of the dimeric urethane) from which the present compounds are derived) comprise about 6 to 24 carbon atoms, wherein the side chain is preferably an unsaturated hydrocarbon.

The viscosity of the compounds of the present invention, and, therefore, the formulations in which they are used, may also readily be adjusted by adding about 0.5% to about 100% by weight of the dimeric urethane, preferably about 1% to about 50% by weight, more preferably about 2% to about 30% by weight, even more preferably about 10% to about 25% by weight of excess unreacted monohydric alcohols to the compounds of the present invention. These unreacted alcohols will reduce the viscosity of the compound or formulation in which they are included for modifying the characteristics of cosmetic, toiletry or personal care products according to the present invention. Unreacted alcohols in the formulation may readily be obtained by including an excess of monohydric alcohol to the diisocyanate before synthesis of the urethane. Alternatively, the addition of monohydric alcohol to the compounds of the invention after synthesis may also represent an appropriate option.

In the present invention, a dimeric urethane compound according to the present invention which is derived from a $C_6$ to $C_{10}$ monohydric alcohol is considered a "light" emollient, i.e., an emollient which has a low viscosity falling within the range of about 10 centipoise units to about 1000 centipoise units. Light emollients are preferably included in personal care products where lower viscosity is a desirable feature. Such personal care products include shampoos, conditioners, fragrances, lotions including sunscreens and suntan lotions. "Heavy" emollients are those dimeric urethane compounds which are derived from monohydric alcohols which are $C_{12}$ or greater in length. Heavy emollients generally have a high viscosity which is above 1000 centipoise units, and preferably fall within the range of about 2000 centipoise units to about 5,000 centipoise units. It is noted that emollients which have viscosities which fall at the upper range of viscosity, i.e., about 5,000 centipoise units and above, in order to be readily workable and useful in the present invention, may need to have their viscosities adjusted by including free monohydric alcohol in an amount up to about 100% by weight of the dimeric urethane compound according to the present invention. Heavy emollients find use in cosmetics and personal care products which require higher viscosities, for example, in creams, ointments, pastes and solid cosmetics such as make-up and lipstick products, deodorants/anti-perspirants, among numerous others.

The following examples of compounds according to the present invention have been prepared:

Monoderm I-24: the reaction product of 2-decyltetradecanol with isophoronediisocyanate (IPDI);

Monoderm I-20: the reaction product of octyldodecanol with IPDI;

Monoderm I-18: the reaction product of isostearyl alcohol with IPDI;

Monoderm I-180: the reaction product of oleyl alcohol with IPDI;

Monoderm I-16: the reaction product of isocetyl alcohol with IPDI;

Monoderm I-14: the reaction product of isotetradeceyl alcohol with IPDI;

Monoderm I-10: the reaction product of isodecyl alcohol with IPDI;

Monoderm N-12: the reaction product of dodecanol with IPDI;

Monoderm 12-3: the reaction product of laureth-3 alcohol with IPDI;

Monoderm N-10: the reaction product of decyl alcohol with IPDI;

Monoderm I-9: the reaction product of isononanol with IPDI;

Monoderm I-8: the reaction product of isooctanol with IPDI;

Monoderm I-6: the reaction product of isohexyl alcohol with IPDI;

Monoderm I-8-C4: the reaction product of Capryl alcohol with IPDI;

Monoderm I-3: the reaction product of isopropanol with IPDI;

Monoderm DGDE: the reaction product of glycol ether dimer with IPDI;

Monoderm N18-100: the reaction product of PEG-100 stearyl ether dimer with IPDI;

Monoderm N4-100: the reaction product of PEG-100 butyl ether dimer with IPDI.

The examples above all use isophorone diisocyanate, but the following isocyanates are among those which may be used to yield acceptable products:
m-phenylenediisocyanate; p-phenylene diisocyanate; 4,4-butyl-m-phenylene diisocyanate;
4-methoxy-m-phenylene diisocyanate; 4-phenoxy-m-phenylene diisocyanate;
4-chloro-m-phenylene diisocyanate; toluenediisocyanate; m-xylylenediisocyanate;
p-xylylenediisocyanate; 1,4-napthalenediisocyanate; cumene-14,-diisocyanate;
durenediisocyanate; 1,5-napthylenediisocyanate; 1,8-napthylenediisocyanate;
1,5-tetrahydronapthylenediisocyanate; 2,6-napthylenediisocyanate;
1,5-tetrahydronapthylenediisocyanate; p,p-diphylenediisocyanate; 2,4-diphenylhexane-1,6-diisocyanate; methylenediisocyanates; ethylenediisocyanates; tri, tetra, penta, hexa, nona and decamethylene diisocyanates; 3-chloro-trimethylenediisocyanate; and 2,3-dimethyltetramethylene diisocyanates.

The present invention also relates to a method of decreasing the viscosity of a urethane compound to be added to a toiletry, cosmetic or personal care product comprising adding a viscosity reducing effective amount of at least one unreacted monohydric alcohol to the urethane compound(s) in an amount ranging from about 0.5% to about 100% by weight of the urethane compound. The compositions which consist essentially of a urethane compound and monohydric alcohol may be added to any number of cosmetic, toiletry and personal care formulations to increase the workability and reduce the viscosity of the formulation.

Listed below are studies comparing the stability of diesters derived from dicarboxylic acids in comparison to difunctional urethanes:

Stability Studies

The following stability study was conducted to determine the structural stability of dimeric urethane compounds according to the present invention compared to mono- and diesters under conditions of pH and thermal variation. Because the decomposition products of the mono- and diesters are alcohol and acid, the degree of decomposition may be accurately determined by measuring the acid value. The measurable decomposition product of the urethane compound is alcohol, which is accurately measured by determining the hydroxyl value.

The following Mono- and diester products were tested:

Isocetyl salicylate (ICSA);

Diisopropyl adipate (DIA);

Diisopropyl dilinoleate (DID);

The following urethane products were tested:

2-ethyl hexanol dimer with IPDI (I-8);

Isocetyl alcohol dimer with IPDI (I-16);

Isostearyl alcohol dimer with IPDI (I-18);

Octyl dodecanol dimer with IPDI (I-20);

Eicosanyl alcohol dimer with IPDI (I-24);

III. Procedure for determining mono- or diester stability

The following steps were performed on each ester sample:

(1) Run acid value test.

(2) Into three ground glass Erlenmeyer flasks A, B, and C, weigh a 20 g sample of the ester.

(3) Into each flask, pipette 50 ml of a neutralized (to phenolpthalein end point) Solution of 70% Isopropanol in water. Boiling stones are added.

(4) Connect flask A to a 4–5 ft. Reflux condenser and heat so that it refluxes 1 ft. high (to approximately 80–90° C.). After connecting flasks A, B and C, proceed to step (7).

(5) Add 10% Aq. Hcl solution to adjust pH of solution in flask B to pH=2.5–3.5. See step (4).

(6) Add 20% Aq. KOH Solution to adjust pH of solution in Flask C to pH=13–14. See step (4).

(7) Reflux for 1 hour.

(8) For each flask, A, B and C, disconnect condenser. Pour Alcoholic solution into wide diameter beaker (A, B and C). Add spin bar. Under hood, evaporate alcohol/water solvent on spin/hot plate until it is reduced to 80–90% of volume. Put beaker in oven (105° C.) until remainder of alcohol/water is evaporated.

(9) Run acid value test on solution in beaker A.

(10) Wash solution in beakers B and C twice with water. Add 20 ml of hot water, mix, add to separatory funnel, drop bottom water layer. Put beakers back into oven until water is evaporated.

(11) Run acid value test on solution in beaker B and solution in beaker C. The acid value method used is A.O.C.S. (AMERICAN OIL CHEMISTS SOCIETY) T.M. #Cd3a-63. SAMPLE SIZE: 10 g±0.1 mg KOH, Aq.: 0.1213N KOH Aq.: 0.4724N IV. Procedure for urethane stability The following steps were performed on each urethane sample:

(1) Run hydroxyl value test.

(2) Follow steps 2–8 for mono- and diester (above).

(3) Run hydroxyl value test on solution in beaker A.

(4) Perform step 10, from above.

(5) Run hydroxyl value test on solution in Beaker B and Beaker C. Hydroxyl value method: A.O.C.S. (AMERICAN OIL CHEMISTS SOCIETY) TM #Cd 13-16. SAMPLE SIZE 10 g±0.1 mg KOH, Aq.= 0.4724N V. Summary of results

| | ESTER STABILITY 1 ACID VALUE UNIT = mg KOH g | | | |
|---|---|---|---|---|
| PRODUCT | ACID V INITIAL mg KOH/g | ACID V Δ = 1 HOUR mg KOH/g "A" | ACID V Δ = 1 HOUR mg KOH/g "B" | ACID V Δ = 1 HOUR mg KOH/g "C" |
| ICSA | 0.91 | 81.6 | 95.3 | 88.6 |
| DIA | 0.26 | 93.1 | 101.2 | 106.3 |
| DID | 0.32 | 41.8 | 62.4 | 58.1 |

A.O.C.S. T.M. # Cd 3a-63
Δ = HEAT/REFLUX

| | Urethane Stability HYDROXYL VALUE UNIT: mg KOH g | | | |
|---|---|---|---|---|
| PRODUCT | HYDROXYL V INITIAL mg KOH/g | HYDROXYL V Δ = 1 HOUR mg KOH/g "A" | HYDROXYL V Δ = 1 HOUR pH = 2.5–3.5 mg KOH g "B" | HYDROXYL V Δ = 1 HOUR pH = 13–14 mg KOH/g "C" |
| I-8 | 10.3 | 11.1 | 10.0 | 10.8 |
| I-16 | 7.3 | 7.9 | 8.1 | 7.1 |
| I-18 | 5.3 | 5.0 | 6.0 | 4.9 |
| I-20 | 16.1 | 15.9 | 16.9 | 16.4 |
| I-24 | 9.3 | 10.1 | 9.9 | 8.9 |

A.O.C.S. T.M.# Cd 13-60
Δ:HEAT/REFLUX

VI. Conclusion of Testing

Under conditions of this study, that is,

"A": Product in alcoholic/water solution, heat

"B": Product in alcoholic/water solution, heat, pH=2.5–3.5

"C": Product in alcoholic/water solution, heat, pH=13–14

The mono and diesters demonostrated less stability than did the dimeric urethane compounds of the present invention to heat and pH chances, whether those changes are primarily acidic or basic.

The present invention is now described, purely by way of illustration, in the following examples. It will be understood by one of ordinary skill in the art that these examples are in no way limiting and that variations of detail can be made without departing from the spirit and scope of the present invention.

Materials and Methods

In performing the following syntheses, the following reagents were used. Solvents, where used, are generally distilled prior to use. 3-isocyanatomethyl-3,5,5-trimethyl cyclohexylisocyanate (IPDI) was obtained from Huls America, Inc., Piscataway, N.J. The monohydric alcohols used in these experiments for condensation with the diiosocyanate were generally obtained from Vista Condea, Houston, Tex. Sources of other materials are indicated in the appropriate experimental section.

EXAMPLE 1

Synthesis of Dimeric Urethane From Isocetyl Alcohol and Isophorone Diisocyanate

To a 1 liter flask equipped with three necks, dropping funnel, nitrogen, heat and vacuum, charge 532 grams(2.2 moles) of isocetyl alcohol. A vacuum of approximately 29 inches is applied and heat is applied to approximately 110° C. to dehydrate the alcohol. Stannous octanoate is added (approximately 1.0 grams), after the temperature is reduced to 40° C. Heat is slowly added to a temperature of 85° C. at which point a nitrogen blanket is placed on the system. Once the temperature has stabilized, a slow addition of 3-isocyanatomethyl-3,5,5-trimethyl cyclohexylisocyanate is added at a rate which maintains the temperature of 85–90° C. A total of 222 grams (1 mol) of the isocyanate is added and once the addition is completed, isocyanate groups are monitored by IR to ensure complete reaction of the alcohol. When the diiosocyanate has been consumed as indicated by IR, the reaction is complete. The temperature of the product is reduced to 60° C., then to room temperature. The product may be used directly without further purification.

EXAMPLE 2

Synthesis of Dimeric Urethane from Isostearyl Alcohol and Isophorone Diisocyanate To a 2 liter flask equipped with a dropping funnel, nitrogen, agitation, heat and vacuum, a charge of 594 grams (2.2 Moles) of isostearyl alcohol was added. A vacuum of approximately 29 inches was applied to remove water with heat application of 110° C. The isostearyl alcohol was then reduced to a temperature of 40° C. and approximately 1.0 gram of stannous octanoate was added. The temperature was brought up to 85° C., nitrogen was introduced as a blanket and a slow addition of isophorone diisocyanate (222 grams, 1 Mol) was initiated in which the rate of addition of the isocyanate was used to maintain a temperature of 85–90° C. in the flask. Once the addition was complete, samples were taken to determine via the use of an infrared that all of the isocyanate was consumed. Any unreacted hydroxyl groups that remain the in flask can be attributed to the excess of isostearyl alcohol that was used to push the reaction to the right.

EXAMPLE 3

Synthesis of Dimeric Urethane from Isocetyl Alcohol and Isophorone Diisocyanate—Excess Isocetyl Alcohol To a 2 liter flask equipped with three necks, a dropping funnel, nitrogen heat and vacuum, charge 532 grams (2.2 moles) of isocetyl alcohol. A vacuum of approximately 29 inches is applied to dehydrate the alcohol and heat is applied to a temperature of 110° C. The temperature is reduced under vacuum to 40° C. and approximately 1.0 grams of stannous octanoate are added. Nitrogen is introduced into the flask and heat is applied to a temperature of approximately 85° C. The heat is turned off and a slow addition of the isophorone diisocyanate is begun such that the temperature is maintained by the addition of the isocyanate in the range of 85–90° C. A total of 222 grams (1 mol) of isophorone diisocyanate is added. Once the addition has been completed, the temperature is maintained at 85–90° C. and the peaks for free isocyanate and free hydroxyl groups are monitored.

EXAMPLE 5

Suntan Lotion (Water Resistant)

| | INGREDIENTS | %, WEIGHT | INCI NAME |
|---|---|---|---|
| A. | Water(Deionized) | 68.6 | |
| | Dowicil-200[1] | 0.2 | Quaternium-15 |
| | Propylene Glycol | 3.0 | Propylene Glycol |
| | Triethanolamine | 0.5 | Triethanolamine |
| B. | Dermol IPM[2] | 5.0 | Isopropyl Myristate |
| | Dermol 20SS[2] | 5.0 | Octyldodecyl Stearoyl Stearate |
| | Dermophos IS-2K[2] | 2.0 | Potassium Isosteareth Phosphate |
| | Monoderm I-16[2] | 3.0 | N/A |
| | Cetyl Alcohol | 0.7 | Cetyl Alcohol |
| | Dermol GMS[2] | 1.5 | Glycerol Stearate |
| | Stearic Acid-TP | 2.0 | Stearic Acid |
| | Dermoblock OS[2] | 5.0 | Octyl Salicylate |
| | Dermoblock MA[2] | 3.5 | Menthyl Anthranilate |
| C. | Color, Fragrance | q.s. | |
| | | 100.0 | |

[1]Dow Chemical
[2]Alzo Inc
Procedure for Preparation:
1. Heat Part A to 50 C.–55 C. with mixing until uniform. 2.
2. Heat Part B to 60 C.–65 C. with mixing until uniform.
3. With good agitation, add Part B to Part A
4. Add Part C

EXAMPLE 6

Sun Protection Cream (Water Resistant)

| | INGREDIENTS | %, WEIGHT | INCI NAME |
|---|---|---|---|
| A. | Water(Deionized) | 67.3 | |
| | Dowicil-200[1] | 0.2 | Quaternium-15 Phosphate |
| | Propylene Glycol | 3.0 | Propylene Glycol |
| | Triethanolamine | 0.8 | Triethanolamine |
| B. | Dermol IPM[2] | 5.0 | Isopropyl Myristate |
| | Dermol 20SS[2] | 4.5 | Octyldodecyl Stearoyl Stearate |
| | Dermophos IS-2K[2] | 2.0 | Potassium Isosteareth Phosphate |
| | Dermol DISD[2] | 3.0 | Diisostearyl Dimer Dilinoleate |
| | Monoderm I-16[2] | 2.0 | N/A |
| | Cetyl Alcohol | 0.7 | Cetyl Alcohol |
| | Dermowax[2] | 1.5 | Glycerol Stearate |
| | Stearic Acid | 2.0 | Stearic Acid |
| | Dermoblock OS[2] | 5.0 | Octyl Salicylate |
| | Dermoblock MA[2] | 3.5 | Menthyl Anthranilate |
| C. | Color, Fragrance | q.s. | |
| | | 100.0 | |

[1]Dow Chemical
[2]Alzo Inc
PROCEDURE:
1. Heat Part A to 50° C.–55° C. with mixing until uniform. 2.
2. Heat Part B to 60° C.–65° C. with mixing until uniform.
3. With constant agitation, add Part B to Part A
5. Add Part C

EXAMPLE 7

Instant Hair Conditioner

| INGREDIENTS | %, WEIGHT | INCI NAME |
|---|---|---|
| PHASE A | | |
| Glycerol | 5.00 | Glyceryl |
| Monoderm I-16 | 0.5 | Bis-(Isocetyl)-3-IPDI Isocyanate |
| Sodium Benzoate | 0.1 | |
| Water | 81.70 | |
| PHASE B | | |
| Dermowax GMS S.E. | 4.00 | Glycerol Monostearate S.E. |
| Cetyl Alcohol | 0.75 | Cetyl Alcohol |
| Stearyl Alcohol | 0.75 | Stearyl Alcohol |
| Lanolin | 1.00 | Lanolin |
| PEG 400 Monooleate | 5.00 | PEG-8 Laurate |
| Neconlo | 1.00 | |
| Perfume | 0.20 | |
| Color, D & C Yellow #5 (1% Solution) | q.s. | |

Procedure:

Heat Phase A with exception of Sodium Benzoate to 180° F. Heat Phase B to 180° F. Add Part B to Part A with agitation. Cool to room temperature, add color, perfume and Sodium Benzoate at 110° F.

EXAMPLE 8

Alcoholic Emulsion #763

| INGREDIENTS | %, WEIGHT | INCI NAME |
|---|---|---|
| PHASE A | | |
| Monoderm I-16 | 1.00 | Bis-(Isocetyl)-3-IPDI Isocyanate |
| Alpine Fragrance #103-601 | 2.00 | |
| Alcohol SDA #40 | 30.00 | |
| PHASE B | | |
| Carbopol 941 (2% Aqueous Solution) (B. F. Goodrich, Inc.) | 30.00 | Carbomer |
| Distilled or Deionized Water | 37.00 | |

Method of Manufacture:

Weigh the ingredients of Phase A into a container of sufficient size to hold the entire batch and stir. Weigh the ingredients for Phase B into a separate container and stir until smooth. Add B to A and stir rapidly until uniform emulsion is formed.

EXAMPLE 9

Bath Gel #766

| INGREDIENTS | %, WEIGHT | INCI NAME |
|---|---|---|
| PHASE A | | |
| TEA Lauryl Sulfate (40%) | 20.00 | Tea Lauryl Sulfate |
| Foamid SLM | 15.00 | Lauramide DEA |
| Monoderm I-16 | 1.00 | Bis-(Isocetyl)-3-IPDI Isocyanate |
| PHASE B | | |
| Methyl Parasept | 0.15 | |
| Propylene Glycol | 1.00 | |
| PHASE C | | |
| PEG 12 | 2.00 | |
| Hydroxy Propyl Methyl Cellulose (3% Aqueous Solution) | 60.35 | |
| PHASE D | | |
| Fragrance | 0.50 | |

Method of Manufacture:

Heat the ingredients of Phase A to 60° C. Dissolve the Methyl Parasept in Propylene Glycol and add to Phase C. Stir mixture of B, C until smooth. Add B, C to A and stir. Then add perfume.

EXAMPLE 10

Dispersible Bath Oil

| INGREDIENTS | %, WEIGHT | INCI NAME |
|---|---|---|
| Monoderm I-16 | 10.00 | Bis-(Isocetyl)-3-IPDI Isocyanate |
| Dermol IPM | 10.00 | Isopropyl Myristate |
| Dermol 1012 | 3.00 | Laureth-2-Octanoate |
| PEG 200 Dilaurate | 4.00 | PEG-4 Laurate |
| Mineral Oil, Light | 69.00 | |
| Fragrance | 4.00 | |

Procedure:

Add all of the oils into a vessel and blend until homogeneous (No heat is necessary). Add the fragrance and continue to mix until the product is clear and uniform. Allow to age 24 hours at room temperature and filter if necessary.

EXAMPLE 11

Cleansing Cream #694

| INGREDIENTS | %, WEIGHT | INCI NAME |
|---|---|---|
| PHASE A | | |
| Beeswax USP Bleached | 15.00 | Besswax |
| Petrolatum White | 15.00 | Petroleum |
| Mineral Oil | 15.00 | Mineral Oil |
| Dermol IPM | 2.00 | Isopropyl Myristate |
| Dermol CP | 1.50 | Cetyl Palmitate |
| Monoderm I-16 | 1.50 | Bis-(Isocetyl)-3-IPDI Isocyanate |
| Methyl Paraben | 0.10 | Methyl Paraben |
| Propyl Paraben | 0.10 | Propyl Paraben |
| Dermol 126 | 1.00 | Laureth-2 Benzoate |
| PHASE B | | |
| Borax USP | 1.25 | Sodium Borate |
| Polysorbate 80 | 0.30 | Polysorbate 80 |
| Glycerin | 3.00 | Glycerin |
| Distilled or Deionized Water | 43.75 | |
| PHASE C | | |
| Perfume | 0.50 | |

EXAMPLE 12

Floating Bath Oil

| INGREDIENTS | %, WEIGHT | INCI NAME |
|---|---|---|
| Monoderm I-16 | 12.00 | Bis-(Isocetyl)-3-IPDI Isocyanate |
| Dermol IPM | 12.00 | Isopropyl Myristate |
| Light Mineral Oil | 71.00 | Mineral Oil |
| Dermol 1012 | 1.00 | Laureth-2-Octanoate |
| Fragrance | 4.00 | |

Procedure:
Add all of the oils into a vessel, and blend until homogeneous (No heat is necessary). Add the fragrance and continue to mix until the product is clear and uniform. Allow to age 24 hours at room temperature and filter if necessary.

EXAMPLE 13

Foot Balm #602

| INGREDIENTS | %, WEIGHT | INCI NAME |
|---|---|---|
| PHASE A | | |
| NECON LO | 0.25 | Dimethyl Lauramine Oleate |
| Squalene | 1.00 | Squalene |
| Stearic Acid T.P. | 2.00 | Stearic Acid |
| Dermowax GMS | 2.50 | Glycerylmonostearate |
| Monoderm I-16 | 4.50 | Bis-(Isocetyl)-3-IPDI Isocyanate |
| Phytostearol Isocyanate | 3.00 | |
| Cetyl Alc. N.F. Flake | 1.00 | Cetyl Alcohol |
| Dermolan GLH | 3.50 | Glycereth-7-Hydroxystearate |
| Dermol 185 | 1.00 | Isostearyl Neopentanoate |
| PHASE B | | |
| Allantoin | 0.20 | |
| Propylene Glycol | 2.00 | |
| Triethanolamine 99% | 1.00 | |
| Preservative Mix (5 parts Methyl parasept to 1 part Propyl Parasept) | 0.25 | |
| Distilled or Deionized Water | 47.03 | |
| PHASE C | | |
| Veegum-5% Slurry | 25.00 | |
| PHASE D | | |
| Alcohol SDA 39C | 5.00 | |
| Menthol U.S.P. | 0.02 | |
| Perfume | 0.75 | |

EXAMPLE 14

Hand And Body Lotion

| INGREDIENTS | %, WEIGHT | INCI NAME |
|---|---|---|
| PHASE A | | |
| Cetyl Alcohol N.F. Flakes | 0.50 | Cetyl Alcohol |
| Dermowax DEGS | 0.50 | Diethylene Glycol Monostearate Pure |
| Stearic Acid T.P. | 2.00 | |
| Triethanolamine 99% N.F. | 0.75 | |
| Beeswax White U.S.P. | 0.50 | |
| Dermol 185 | 2.00 | Isostearyl Neopentanoate |

-continued

| INGREDIENTS | %, WEIGHT | INCI NAME |
|---|---|---|
| PHASE B | | |
| Propylene Glycol | 2.00 | |
| Sorbitol (70%) | 2.00 | |
| Allantoin | 0.20 | |
| Preservative | 0.25 | |
| Distilled or Deionized Water | 70.55 | |
| Monoderm I-16 | 1.00 | Bis-(Isocetyl)-3-3IPDI Isocyanate |
| PHASE C | | |
| Carbopol 941 | 10.00 | Carbomer |
| PHASE D | | |
| Veegum (0.5% Aqueous) | 7.50 | |
| PHASE E | | |
| Perfume | 0.25 | |

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed:

1. A diurethane emollient compound for use in treating keratinous or epithelial tissue including skin, hair, nails and mucous membranes according to the formula:

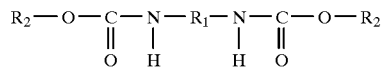

where $R_1$ is selected from a group of saturated or unsaturated linear, cyclic and branch-chained hydrocarbons; and $R_2$ are the same or different and are selected from the group consisting of $C_6$ to $C_{50}$ linear, cyclic, aromatic or branch-chained hydrocarbons and $C_6$ to $C_{50}$ linear, cyclic or branched-chain aminoalkyl groups.

2. The compound according to claim 1 wherein $R_2$ is a $C_6$ to $C_{36}$ linear or branch-chained hydrocarbon group.

3. The compound according to claim 1 wherein $R_1$ is obtained from a monohydric alcohol selected from the group consisting of 2-decyltetradecanol, octyldodecanol, isostearyl alcohol, oleyl alcohol, isocetyl alcohol, isotetradecyl, isodecyl alcohol, dodecanol, laureth-3 alcohol, decyl alcohol, isoctanol, n-stearyl alcohol, iso-stearyl alcohol, arachidyl alcohol, isononanol, isohexyl alcohol and capryl alcohol.

4. The compound according to claim 1 wherein $R_2$ is a $C_{10}$ to $C_{24}$ linear or branch-chained hydrocarbon.

5. The compound according to claim 1 wherein $R_2$ is a $C_6$ to $C_{10}$ hydrocarbon.

6. The compound according to claim 1 wherein $R_1$ is isophorone.

7. The compound according to claim 1 wherein $R_1$ is isophorone.

8. The compound according to claim 3 wherein $R_1$ is isophorone.

9. The compound according to claim 4 wherein $R_1$ is isophorone.

10. The compound according to claim 5 wherein $R_1$ is isophorone.

11. The compound according to claim 1 wherein $R_1$ is isophorone.

12. The compound of claim 1, wherein $R_2$ is from about 6 to about 36 carbon atoms in length.

13. The compound according to claim 1, wherein $R_2$ is from about 6 to about 12 carbon atoms in length.

14. The compound of claim 1, wherein $R_2$ is from about 6 to about 24 carbon atoms in length.

15. The compound according to claim 1, wherein $R_2$ is from about 12 to about 36 carbon atoms in length.

16. The compound according to claim 1, wherein $R_2$ is from about 20 to about 36 carbon atoms in length.

17. The compound according to claim 1, wherein $R_1$ is selected from the group consisting of isophorone; m-phenylene; p-phenylene; 4,4-butyl-m-phenylene; 4-methoxy-m-phenylene; 4-phenoxy-m-phenylene; 4-chloro-m-phenylene; toluene; m-xylylene; p-xylylene; 1,4-napthalene; cumene-1,4-; durene; 1,5-napthylene; 1,8-napthylene; 1,5-tetrahydronapthylene; 2,6-napthylene; p,p-diphenylene; 2,4-dephenylhexane-1,6-; methylene; ethylene; tri, tetra, penta, hexa, nona and decamethylene; 3-chloro-trimethylene; and 2,3-dimethyltetramethylene.

18. The compound according to claim 17, wherein $R_1$ is isophorone.

19. The compound according to claim 1, wherein $R_2$ is selected from the group consisting of 2-decyltetradecane, octyldodecane, isostearene, olene, isocetene, dodecane, laurene, decane, isononane, octane, isohexane and caprene.

20. The compound according to claim 1 further comprising about 0.5% to about 50% by weight of a free or unreacted monohydric alcohol $R_2OH$.

* * * * *